United States Patent
Doshi et al.

(10) Patent No.: US 6,878,694 B2
(45) Date of Patent: Apr. 12, 2005

(54) OPHTHALMIC IRRIGATING SOLUTION ADAPTED FOR USE IN LASIK SURGERY

(75) Inventors: Uday Doshi, Randolph, NJ (US); Kerry L. Markwardt, Mansfield, TX (US); Pao-Li Wang, Fort Worth, TX (US); Emerson Maddox, Forth Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/432,273

(22) PCT Filed: Nov. 29, 2001

(86) PCT No.: PCT/US01/44526
§ 371 (c)(1),
(2), (4) Date: May 19, 2003

(87) PCT Pub. No.: WO02/49610
PCT Pub. Date: Jun. 27, 2002

(65) Prior Publication Data
US 2004/0033960 A1 Feb. 19, 2004

Related U.S. Application Data

(60) Provisional application No. 60/257,571, filed on Dec. 20, 2000.

(51) Int. Cl.[7] .................... A61K 31/70; A61K 31/74; A61K 31/728; A61K 31/736
(52) U.S. Cl. ................ 514/54; 514/23; 514/55; 514/57
(58) Field of Search ................. 514/23, 54, 55, 514/57, 21; 424/78.18

(56) References Cited

U.S. PATENT DOCUMENTS

| | | |
|---|---|---|
| 4,255,415 A | 3/1981 | Chrai et al. |
| 4,271,143 A | 6/1981 | Schoenwald et al. |
| 4,550,022 A | 10/1985 | Garabedian et al. |
| 4,861,760 A | 8/1989 | Mazuel et al. |
| 5,106,615 A | 4/1992 | Dikstein |
| 5,133,708 A | 7/1992 | Smith |
| 5,277,911 A | 1/1994 | Viegas et al. |
| 5,318,780 A | 6/1994 | Viegas et al. |
| 5,409,904 A * | 4/1995 | Hecht et al. ............... 514/23 |
| 5,578,578 A | 11/1996 | Hecht et al. |
| 5,587,175 A | 12/1996 | Viegas et al. |
| 5,710,148 A | 1/1998 | Sudo et al. |
| 5,728,405 A | 3/1998 | McDonnell |
| 5,770,628 A | 6/1998 | Cantoro |
| 5,861,955 A | 1/1999 | Gordon |
| 5,871,772 A * | 2/1999 | Cantoro ............... 424/427 |
| 5,958,443 A | 9/1999 | Viegas et al. |

FOREIGN PATENT DOCUMENTS

| | | | |
|---|---|---|---|
| EP | 0 517 970 | 12/1992 | |
| EP | 0517970 | * 12/1992 | .......... A61K/31/73 |
| GB | 2 196 255 | 4/1988 | |
| WO | WO 94/10976 | 5/1994 | |
| WO | WO 95/13768 | 5/1995 | |
| WO | WO 97/28787 | 8/1997 | |
| WO | WO 98/08048 | 2/1998 | |
| WO | WO 98/29069 | 7/1998 | |
| WO | WO 98/37903 | 9/1998 | |
| WO | WO 99/06023 | 2/1999 | |
| WO | WO 99/51273 | 10/1999 | |
| WO | WO 02/24116 | 3/2002 | |

OTHER PUBLICATIONS

Pallikaris, et al., "*Laser In–Situ Keratomileusis*", Lasers in Surgery and Medicine, vol. 10; pp. 463–468; (1990).
Farah, et al., "*Laser In–Situ Keratomileusis: Literature Review of a Developing Technique*"; Journal of Cataract and Refractive Surgery, vol. 24; pp. 989–1006; (Jul. 1998).
Gimbel, et al., "*Indications, Results, and Complications of LASIK*", Current Opinion in Ophthalmology; vol. 9; pp. 3–8 (1998).
Carr, et al., "*Laser In–Situ Keratomileusis*", Ophthalmology Clinics of North America, vol. 10; pp. 533–542; No. 4; (Dec. 1997).
Hatsis, "*80% Balanced Salt Solution to Reduce Post–LASIK Flap Striae and Wrinkles*", Symposium on Cataract, IOL and Refractive Surgery, Ameican Society of Cataract and Refractive Surgery, Apr. 10–14, 1999.
Wilson, "*LASIK Surgery*", AORN Journal, vol. 71, pp. 963–983; (2000).

* cited by examiner

Primary Examiner—James O. Wilson
Assistant Examiner—Ganapathy Krishnan
(74) Attorney, Agent, or Firm—Gregg C. Brown

(57) ABSTRACT

Compositions and methods for facilitating the formulation and closure of a corneal flap during LASIK surgery are described. The compositions and methods are based on the use of one or more viscosity-enhancing agents (e.g., chondroitin sulfate) to provide an ophthalmic irrigating solution with improved coating properties and prolonged dwelling time on the cornea, thereby providing lubrication for the microkeratome used to form the corneal flap, reduce corneal epithelial abrasions, and help to produce smooth and consistent cuts with the microkeratome blade.

9 Claims, No Drawings

US 6,878,694 B2

OPHTHALMIC IRRIGATING SOLUTION ADAPTED FOR USE IN LASIK SURGERY

This application claims priority from International Patent Application No. PCT/US01/44526 filed on Nov. 29, 2001, which claims priority from U.S. Provisional Application Ser. No. 60/257,571, filed on Dec. 20, 2000.

BACKGROUND OF THE INVENTION

The present invention is directed to the field of ophthalmic surgery. More specifically, the invention is directed to an irrigating solution that may be utilized during various ophthalmic procedures, but is particularly useful in facilitating the formation and subsequent closure of a corneal flap during laser in situ keratomileusis ("LASIK").

LASIK surgery involves the use of a microkeratome to make an incision in the cornea transverse to the optical axis. This incision results in the formation of a corneal flap which is temporarily lifted and folded back so as to expose underlying tissue which is then sculpted or ablated with a laser so as to modify the curvature of the cornea and thereby correct the vision of the patient. For further background regarding LASIK surgery, in particularly the formation of the corneal flap by means of a microkeratome, please refer to the following publications:

Pallikaris et al., "Laser In-Situ Keratomileusis", Lasers in Surgery and Medicine, volume 10, Pages 463–468 (1990);

Carr et al., "Laser In-Situ Keratomileusis", Ophthalmology Clinics of North America volume 10, pages 533–543 (1997);

Gimbel et al., "Indications, Results, and Complications of LASIK", Current Opinion in Ophthalmology, volume 9, pages 3–8 (1998);

Farah et al., "Laser In-Situ Keratomileusis: Literature Review of a Developing Technique" Journal of Cataract and Refractive Surgery, volume 24, pages 1059–1063 (1998); and Wilson, "LASIK Surgery", AORN Journal, volume 71, pages 963–983 (2000).

Although the LASIK surgical procedure has now been conducted on thousands of patients, certain aspects of the procedure occasionally give rise to complications. The formation of the corneal flap is one aspect of the overall LASIK procedure which can give rise to complications. Specifically, the formation of the corneal flap can result in epithelial abrasions or other damage due to the microkeratome blade, and the cut or incision by means of the microkeratome blade can sometimes be somewhat unpredictable. Moreover, in some patients, corneal haze or edema subsequent to surgery and flap wrinkles or curled flap edges have been attributed to problems in forming the corneal flap with the microkeratome. The failure of the flap to reseal following surgery is also a significant complication, because such failure creates a greater risk of infection and may adversely affect visual acuity.

In view of the foregoing, there is a need for products which will enhance the ability of surgeons to form the corneal flap without damaging the cornea or associated ophthalmic tissues. In particular, there is a need for products which: (1) help to minimize corneal epithelial abrasions; (2) facilitate smooth, consistent cuts; and (3) expedite postoperative visual acuity by facilitating formation of a flap that is not wrinkled, fits well upon replacement, seals readily following the LASIK procedure and adheres to the adjacent corneal tissue.

Various types of solutions are currently being applied to the cornea prior to use of the microkeratome to form the corneal flap in LASIK surgical procedures. However, none of these solutions has been specifically designed or adapted to meet the needs of the ophthalmic surgeon in conjunction with LASIK surgery. Consequently, each of these solutions has one or more drawbacks. For example, some of the solutions provide adequate lubrication, but contain other ingredients (e.g., antimicrobial preservatives) which are potentially toxic to the cornea and therefore highly undesirable in conjunction with an invasive surgical procedure such as LASIK surgery. Thus, the solutions currently being utilized are, at best, less than ideal.

SUMMARY OF THE INVENTION

The present invention provides an improved irrigating solution for topical application to the cornea in conjunction with ophthalmic surgical procedures, particularly the formation and subsequent sealing of a corneal flap in conjunction with LASIK surgery. The solution comprises a viscosity-enhancing agent and an ophthalmically acceptable aqueous vehicle.

The solutions of the present invention contain a viscosity-enhancing agent to modify the lubricity or tackiness of the solution upon application to the cornea. The viscosity-enhancing agent provides the irrigating solution with better coating properties and prolonged dwelling time on the surface of the cornea. This facilitates formation of the corneal flap with less force and less potential damage to the tissues from either the microkeratome blade or the vacuum ring utilized to hold the cornea in place during formation of the corneal flap.

The viscosity-enhancing agent provides the irrigating solutions with a mild adhesive or glue-like property that facilitates the closure and sealing of the corneal flap following completion of the LASIK procedure.

The solution can be either isotonic, mildly hypotonic, or mildly hypertonic. The osmolality of the solutions can be modified so as to affect the size of the flap and thereby facilitate either the formation of the flap, the removal of wrinkles from the flap, or replacement and sealing of the flap. A hypotonic solution may be utilized to expand the flap, as a result of the uptake of fluid by the flap, and thereby remove wrinkles from the flap. A hypertonic solution may be utilized to contract the flap, as a result of loss of fluid from the flap, and thereby facilitate replacement and sealing of the flap, as well as adherence of the flap to adjacent tissue.

Various types of vehicles for the viscosity-enhancing agent may be utilized. However, the vehicle preferably contains electrolytes, a buffer (e.g., bicarbonate, phosphate or a combination thereof), and an energy source. These agents help to maintain the normal function of corneal tissues during the surgical procedure and promote a rapid recovery of visual acuity subsequent to the surgery.

The solutions of the present invention are sterile, and preferably do not contain antimicrobial preservatives (e.g., benzalkonium chloride). Such preservatives are potentially harmful to the cornea, particularly in patients undergoing LASIK surgery.

DETAILED DESCRIPTION OF THE INVENTION

The irrigating solutions of the present invention contain a small amount of a viscosity-enhancing agent. This key component of the solutions facilitates several aspects of the LASIK procedure. Specifically, the viscosity-enhancing agent provides the irrigating solutions with better coating properties and prolonged dwelling time on the corneal surface, thereby providing lubrication for the microkeratome, reducing corneal epithelial abrasions, and helping to produce smooth and consistent cuts with the microkeratome blade. The viscosity-enhancing agent also provides the irrigating solutions with a mild adhesive or glue-like property, which facilitates the retention of the solution on the cornea and helps to seal the flap following the LASIK procedure.

The viscosity-enhancing agent is preferably a polymeric material. Various pharmaceutically acceptable polymeric materials can be used for this purpose. The preferred polymeric materials include: chondroitin sulfate, sodium hyaluronate or other proteoglycans; cellulose derivatives, such as hydroxypropyl methylcellulose ("HPMC"), carboxy methylcellulose ("CMC"), and hydroxyethyl cellulose ("HEC"); collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); xanthan gum; gellan gums; alginate; chitosans; polyvinyl alcohol; carboxyvinyl polymers (e.g., carbomers such as the Carbopol™ brand polymers available from B. F. Goodrich); and various other viscous or viscoelastomeric substances, including but not limited to those described in U.S. Pat. No. 5,409,904 (Hecht, et al.), the entire contents of which are hereby incorporated by reference in the present specification.

The following patent publications may be referred to for further details concerning the above-listed viscosity-enhancing agents: U.S. Pat. No. 4,861,760 (gellan gums); U.S. Pat. No. 4,255,415 and WIPO Publication No. WO 94/10976 (polyvinyl alcohol); U.S. Pat. No. 4,271,143 (carboxyvinyl polymers); WIPO Publication No. WO 99/51273 (xanthan gum); and WIPO Publication No. WO 99/06023 (galactomannans). The entire contents of the foregoing references pertaining to the structures, chemical properties and physical properties of the respective viscosity enhancing agents described above are hereby incorporated in the present specification by reference.

The most preferred viscosity-enhancing agent is chondroitin sulfate. The use of chondroitin sulfate in an amount of 0.1 to 10 w/v % allows the above-stated objectives to be achieved. Moreover, the use of chondroitin sulfate is also advantageous in that it can serve not only as the viscosity-enhancing agent, but also as an osmolality-enhancing agent.

The viscosity-enhancing agent modifies the lubricity or tackiness of the irrigating solutions so as to facilitate the formation of the corneal flap with less force applied to the microkeratome blade, and also help prevent damage to ophthalmic tissue from the blade or the vacuum ring. Also, as indicated above, the viscosity-enhancing agent provides the irrigating solutions with a mild adhesive or glue-like property to facilitate the closure and sealing of the corneal flap. The amount of viscosity-enhancing agent required in order to achieve these objectives is referred to herein as "an effective amount". The amount of viscosity-adjusting agent required will vary depending on the polymeric material or combination of materials selected in a given case and other considerations. However, the concentration of the viscosity-enhancing agent in the irrigating solutions of the present invention will generally be in the range of from about 0.1 to about 10 weight/volume percent ("w/v %").

The amount of viscosity-enhancing agent utilized will generally be an amount sufficient to achieve a slight to moderate increase in viscosity, relative to the viscosity of the same solution prior to the addition of the viscosity-adjusting agent. However, in some cases the increase in viscosity may be so slight as to be immeasurable with conventional laboratory equipment. The viscosities of the irrigating solutions of the present invention will generally be in the range of 1 to 50 centipoises ("cps"), preferably 3 to 30 cps.

The irrigating solutions of the present invention are sterile and preferably do not contain antimicrobial preservatives such as benzalkonium chloride. The solutions that do not contain such preservatives are referred to herein as being "unpreserved".

The above-described viscosity-enhancing agents are contained in an aqueous, ophthalmically acceptable vehicle. The vehicle preferably contains electrolytes and other components to maintain the normal function of corneal tissues during ophthalmic surgical procedures. The preferred vehicle is a balanced salt solution, such as BSS™ (Balanced Salt Solution) Sterile Irrigating Solution manufactured by Alcon Laboratories, Inc. (Fort Worth, Tex.), or BSS PLUS® (Balanced Salt Solution) Sterile Irrigating Solution, also manufactured by Alcon Laboratories, Inc. However, the invention is not limited relative to the types of balanced salt solutions or other electrolyte/nutrient solutions that may be utilized to form the enhanced viscosity irrigating solutions described herein.

As indicated above, the irrigating solutions of the present invention can be either isotonic, mildly hypotonic, or mildly hypertonic. The osmolalities of the solutions will typically be in or near the range of 200 to 400 milliosmoles per kilogram water ("mOsm/kg"). The isotonic solutions will generally have osmolalities in or near the range of 280 mOsm to 320 mOsm, while the mildly hypotonic and mildly hypertonic solutions will have osmolalities below and above this range, respectively.

As will be understood by those skilled in the art, the osmolalities of the irrigating solutions of the present invention are directly dependent on the types and amounts of solutes present. The osmolalities can be lowered by reducing the amount of solutes present and/or increasing the amount of solvent. Conversely, the osmolalities can be raised by increasing the amount of solutes present and/or reducing the amount of solvent. The solutes that can be utilized to adjust osmolality include: ionic salts, such as sodium chloride and potassium chloride; nonionic polyhydric alcohols, such as glycerol and mannitol; and various other agents known to those skilled in the art.

In a preferred embodiment of the present invention, the solutions are formulated to be mildly hypertonic. It has been found that the mildly hypertonic solutions are particularly useful in facilitating replacement and adhesion of the corneal flap following the photoablation step of the LASIK procedure. As utilized herein, the phrase "mildly hypertonic" refers to solutions having osmolalities in excess of 300 mOsm/kg. The osmolalities of the mildly hypertonic solutions of present invention will generally be in the range of 300 to 400 mOsm. [Note: Is this range appropriate?]

The irrigating solutions of the present invention may be utilized in conjunction with various types of ophthalmic surgical procedures, but are particularly adapted for use in LASIK surgery. The solutions may be utilized to facilitate formation of the corneal flap by applying a few drops of the solutions to the cornea immediately before the microkeratome is applied to the cornea. The solutions may also be utilized to facilitate closure and sealing of the corneal flap following the photoablation step of the LASIK procedure.

This use of the solutions is typically performed by irrigating the cornea below the flap and around the periphery of the flap for a period of about 2 to 5 minutes.

The following examples are provided to further illustrate the irrigating solutions of the present invention.

EXAMPLE 1

| Ingredient | Amount (w/v %) |
| --- | --- |
| Chondroitin sulfate | 0.1–10 |
| Sodium Chloride | 0.2–0.8 (to adjust tonicity) |
| Potassium chloride | 0.075 |
| Calcium chloride | 0.048 |
| Magnesium chloride | 0.03 |
| Sodium citrate | 0.17 |
| Sodium acetate | 0.39 |
| Hydrochloric acid/Sodium hydroxide | qs to pH 6.5–8.5 |
| Purified water/Water for injection | qs to volume |

One liter of the above-described solution is prepared by dissolving 0.75 grams potassium chloride, 0.48 grams of calcium chloride, 0.3 grams of magnesium chloride, 1.7 grams of sodium citrate and 3.9 grams of sodium acetate in water for injection at about 20° C. The sodium chloride is then added and dissolved to adjust the osmolality of the solution to the desired level. Chondroitin sulfate is then added to the solution to make the concentration of chondroitin sulfate in the range of 0.1 to 10% weight by volume. The pH of the solution is adjusted to about 7.4 by adding 1N HCl or 1N NaOH. Additional water for injection is then added to bring the solution to its final volume.

EXAMPLE 2

| Ingredient | Amount (w/v %) |
| --- | --- |
| Chondroitin sulfate | 0.1–10 |
| Sodium Chloride | 0.2–0.8 (to adjust tonicity) |
| Potassium chloride | 0.038 |
| Calcium chloride | 0.0154 |
| Magnesium chloride | 0.02 |
| Sodium bicarbonate | 0.21 |
| Dextrose | 0.09 |
| Oxidized glutathione | 0.0184 |
| Dibasic sodium phosphate | 0.04 |
| Hydrochloric acid and/or | qs to adjust pH |
| Sodium hydroxide | qs to adjust pH |
| Water for injection | qs to volume |

One liter of the above-described solution is prepared by dissolving 0.38 grams potassium chloride, 0.154 grams of calcium chloride, 0.2 grams of magnesium chloride and 0.9 grams of dextrose in water for injection at about 20° C. The sodium chloride is then added and dissolved to adjust the osmolality of the solution to the desired level. Then 0.4 grams of dibasic sodium phosphate is added and dissolved. Chondroitin sulfate is added to the solution to make the concentration of chondroitin sulfate in the range of 0.1 to 10% weight by volume. Oxidized glutathione in the amount of 0.184 grams and 2.1 grams of sodium bicarbonate are then added and dissolved. The pH of the solution is adjusted to about 7.4 by adding 1N HCl or 1N NaOH. Additional water for injection is added to bring the solution to its final volume.

Further details concerning irrigating solution vehicles of the types described in Example 2 above are provided in U.S. Pat. No. 4,550,022 (Garabedian, et al.), the entire contents of which are hereby incorporated in the present specification by reference. As explained in the Garabedian, et al. patent, it is sometimes necessary to provide irrigating solutions in the form of two or more separate solutions that are combined just prior to use. The irrigating solutions of the present invention may be provided in this form, if necessary to maintain the chemical stability of certain key components or avoid potential chemical interactions between components during extended periods of storage.

We claim:

1. A method of facilitating the formation of a corneal flap during a LASIK surgical procedure by means of a microkeratome and facilitating the closure and sealing of the corneal flap following completion of the photoablation step of the LASIK procedure, which comprises applying an ophthalmic irrigating solution to the corneal surface immediately before the microkeratome is applied to the eye to facilitate formation of the corneal flap and irrigating the cornea below the flap and around the periphery of the flap subseguent to the photoablation step, said solution comprising a viscosity-enhancing agent in an amount effective to enhance the viscosity of the solution, and an ophthalmically acceptable aqueous vehicle for said viscosity-enhancing agent.

2. A method according to claim 1, wherein the irrigating solution has a viscosity of 1 to 50 cps.

3. A method according to claim 1, wherein the viscosity-enhancing agent is selected from the group consisting of: proteoglycans; cellulose derivatives; collagen or modified collagen; galactomannans; xanthan gum; gellan gum; alginate; chitosans; polyvinyl alcohol; and carboxyvinyl polymers.

4. A method according to claim 3, wherein the viscosity-enhancing agent comprises a proteoglycan.

5. A method according to claim 4, wherein the proteoglycan is selected from the group consisting of chondroitin sulfate and sodium hyaluronate.

6. A method according to claim 5, wherein the viscosity-enhancing agent comprises chondroitin sulfate.

7. A method according to claim 1, wherein the irrigating solution is sterile and unpreserved.

8. A method according to claim 7, wherein the ohthalmically acceptable aqueous vehicle comprises a balanced salt solution containing electrolytes, a buffer and an energy source.

9. A method according to claim 1, wherein the irrigating solution has a Viscosity of 3 to 30 cps.

* * * * *